(12) United States Patent
Alami

(10) Patent No.: US 11,975,119 B2
(45) Date of Patent: May 7, 2024

(54) BREATHING TREATMENT APPARATUS

(71) Applicant: Fisher & Paykel Healthcare Limited, Auckland (NZ)

(72) Inventor: Nordyn Alami, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 47 days.

(21) Appl. No.: 17/842,567

(22) Filed: Jun. 16, 2022

(65) Prior Publication Data

US 2022/0305163 A1     Sep. 29, 2022

Related U.S. Application Data

(63) Continuation of application No. 16/327,159, filed as application No. PCT/NZ2017/050124 on Sep. 22, 2017, now Pat. No. 11,395,859.

(Continued)

(51) Int. Cl.
*A61M 16/00*     (2006.01)
*A61L 2/10*     (2006.01)
(Continued)

(52) U.S. Cl.
CPC .................... *A61L 2/24* (2013.01); *A61L 2/10* (2013.01); *A61L 2/26* (2013.01); *A61M 16/0051* (2013.01); *A61M 16/0066* (2013.01); *A61M 16/16* (2013.01); *C12Q 1/04* (2013.01); *A61L 2202/11* (2013.01); *A61L 2202/14* (2013.01); *A61L 2202/24* (2013.01); *A61L 2209/111* (2013.01); *A61M 2202/203* (2013.01); *A61M 2205/0205* (2013.01); *A61M 2205/11* (2013.01); *A61M 2205/3303* (2013.01); *A61M 2205/581* (2013.01); *A61M 2205/583* (2013.01); *A61M 2205/60* (2013.01); *A61M 2205/6018* (2013.01);
(Continued)

(58) Field of Classification Search
CPC ..... A61L 2/24; A61L 2/10; A61L 2/26; A61L 2202/11; A61L 2202/14; A61L 2209/111; C12Q 1/04; A61M 16/0051; A61M 16/0066; A61M 16/16; A61M 2202/203; A61M 2205/0205; A61M 2205/11; A61M 2205/3303; A61M 2205/581; A61M 2205/583; A61M 2205/60; A61M 2205/6018; A61M 2205/7563; A61M 2209/10

See application file for complete search history.

(56) References Cited

U.S. PATENT DOCUMENTS 8,373,206 B2    2/2013    Potter
9,204,821 B2    12/2015    Martino et al.
(Continued)

FOREIGN PATENT DOCUMENTS

CA          2919371        7/2016
WO    WO 2012/064366      5/2012
(Continued)

OTHER PUBLICATIONS

International Search Report, Application No. PCT/NZ2017/050124, dated Dec. 22, 2017, in 9 pages.

*Primary Examiner* — Steven O Douglas
(74) *Attorney, Agent, or Firm* — Knobbe Martens Olson and Bear, LLP

(57) ABSTRACT

A breathing treatment apparatus delivers breathing gas to a user. The apparatus may be configured to comprise one or more sensors for sensing microbial growth within the apparatus.

19 Claims, 7 Drawing Sheets

Related U.S. Application Data

(60) Provisional application No. 62/398,087, filed on Sep. 22, 2016.

(51) Int. Cl.
*A61L 2/24* (2006.01)
*A61L 2/26* (2006.01)
*A61M 16/16* (2006.01)
*C12Q 1/04* (2006.01)

(52) U.S. Cl.
CPC . *A61M 2205/7563* (2013.01); *A61M 2209/10* (2013.01)

(56) References Cited

U.S. PATENT DOCUMENTS

| | | |
|---|---|---|
| 2004/0141875 A1 | 7/2004 | Doshi |
| 2005/0190058 A1 | 9/2005 | Call |
| 2007/0209143 A1 | 9/2007 | Choi et al. |
| 2014/0131595 A1 | 5/2014 | Nathan et al. |
| 2014/0364758 A1 | 12/2014 | Schindhelm et al. |
| 2015/0056686 A1 | 2/2015 | Potter |
| 2016/0193437 A1 | 7/2016 | Bao et al. |

FOREIGN PATENT DOCUMENTS

| | | |
|---|---|---|
| WO | WO 2014/120024 | 8/2014 |
| WO | WO 2016/086273 | 6/2016 |

BREATHING TREATMENT APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention generally relates to respiratory devices. More particularly, the present invention relates to respiratory devices for humidifying breathing gases.

DESCRIPTION OF THE RELATED ART

Breathing treatment devices, such as continuous positive airway pressure (CPAP) machines, typically include an airflow generator to supply pressurised breathing gases. In some breathing treatment devices, an integrated humidification compartment may be provided, or alternatively a humidifier may be provided separately for connection to the breathing treatment device. The humidification compartment is configured to receive a humidification chamber that may contain a supply of water that is used to humidify breathing gases supplied by the breathing treatment device to a user.

It can be important for breathing treatment devices to be kept as clean as possible, especially areas of the device that contact water used to humidify breathing gases and those areas of the device that contact the humidified breathing gases. This is because bacteria may be found in water within the humidification chamber and bacterial growth may be particularly common in moist or humid environments, such as in the breathing tube and in the humidification compartment of a breathing treatment device. Other sources of bacteria include patient exhalation and patient handling of the humidification chamber, breathing tube, and other components of the device. By maintaining the cleanliness of the device, there is a reduced risk that pathological bacteria may infect the breathing gases that are then inhaled by the user. It is therefore common for manufacturers of breathing treatment devices to recommend a standardised regular regime for cleaning the device. Typically, a user is required to clean particular components of the device daily and to thoroughly clean the humidification chamber weekly, regardless of the frequency or duration of use of the apparatus. Compliance with the cleaning regime is important for the user's health, but the cleaning regime is typically prescriptive, time-consuming, and relatively labour intensive, which may reduce compliance levels. It is possible that such a rigid cleaning regime may not be necessary for all patients, as some patients may use the device more regularly or for longer periods than others. A more personalised cleaning regime may therefore be useful to encourage compliance with cleaning requirements. If the burden of cleaning the device may be minimised through a more personalised cleaning regime, it may be possible to also increase user compliance with breathing treatment therapy.

It is therefore an object of the present invention to: (a) provide a breathing treatment device, such as a CPAP machine, that is configured to provide a user with an indication that bacteria has been detected in at least one location on the device; or (b) to at least provide a useful alternative to known breathing treatment devices.

SUMMARY OF THE INVENTION

CPAP machines include an airflow generator to supply pressurised gas to a user. Many CPAP machines include a heated water reservoir or other source of water for humidification of the pressurised gas.

Water, damp areas, and particularly heated damp areas tend to be prone to microbial growth, such as bacterial growth or fungal growth. If high levels of pathogenic bacterial growth form in a CPAP machine, it is possible for the bacteria to infect the breathing gases delivered by the machine to the user, resulting in a risk to the user's health.

In some configurations, the present invention comprises a breathing treatment apparatus configured to provide an indication of the presence of bacteria in one or more components of the apparatus. A user receiving the indication may then know when to clean the apparatus. In this way, the apparatus may be used to provide a personalised cleaning regime that may reduce the extent and/or frequency of cleaning required, where applicable, to increase user compliance with cleaning requirements and with breathing treatment therapy. The personalised cleaning regime may also provide an indication of which component(s) of the apparatus may require more regular cleaning or, in some cases, replacement.

In one aspect, the invention provides a breathing treatment apparatus for the delivery of breathing gas to a user, wherein the apparatus comprises at least one bacteria sensor configured to detect the presence of bacteria in the apparatus and to provide an indication to a user that bacteria is present. Preferably, the indication is a visual or audio alert.

The bacteria sensor may be an electronic sensor configured to detect the presence of bacteria on or near the sensor. For example, the sensor may be a smell sensor configured to detect odours caused by bacterial colonies.

Alternatively, the bacteria sensor may be a physical sensor configured to indicate the presence of bacteria on the sensor.

In one form, the apparatus comprises a control system configured to receive a signal from the at least one sensor when the sensor detects the presence of bacteria in the apparatus and to generate an alert that causes a visual indication to be displayed on a user interface. The user interface may form part of the breathing treatment apparatus. Alternatively, the user interface may form part of a remote device, such as a computer or smartphone.

In one form, the electronic sensor comprises an electronic sensor ID that is associated with a positioning code that indicates the location of the sensor in the breathing treatment apparatus and wherein the control system is configured to receive a signal from the electronic sensor and to generate an indication in the form of an alert that provides a visual indication that identifies the component of the breathing treatment apparatus in which the sensor, and therefore the bacteria, is located and that needs to be cleaned.

The apparatus optionally comprises a sterilisation system for sterilising the interior of the apparatus.

The control system may be configured to automatically activate the sterilisation system upon receiving a signal from a bacteria sensor that the presence of bacteria has been detected in the apparatus and that the bacteria detected is in a quantity exceeding a predetermined threshold. Preferably, the control system automatically activates the sterilisation system upon receiving such a signal from the bacteria sensor and after the control system has also determined that the breathing treatment apparatus is off or not providing therapy. Optionally, the sterilisation system comprises a manual control that a user may operate to activate the sterilisation system manually. Alternatively, the control system may automatically activate the sterilisation system at the end of a therapy session, at a set time after a therapy session has ended, or at a set time of day.

In another aspect, the invention provides a sensing tool configured to receive at least one bacteria sensor, wherein the tool is configured to be used to sense bacterial growth on a component part of a breathing treatment apparatus or within water held in a humidification chamber of a breathing treatment apparatus and wherein the at least one sensor is configured to be exposed to possible bacterial growth for a minimum predetermined period of time. The bacteria sensor may be an electronic sensor and/or a physical sensor.

BRIEF DESCRIPTION OF THE DRAWINGS

These and other features, aspects and advantages of the present invention will be described with reference to preferred embodiments shown in the following drawings, in which.

DETAILED DESCRIPTION OF THE PREFERRED EMBODIMENTS

Figure 1:
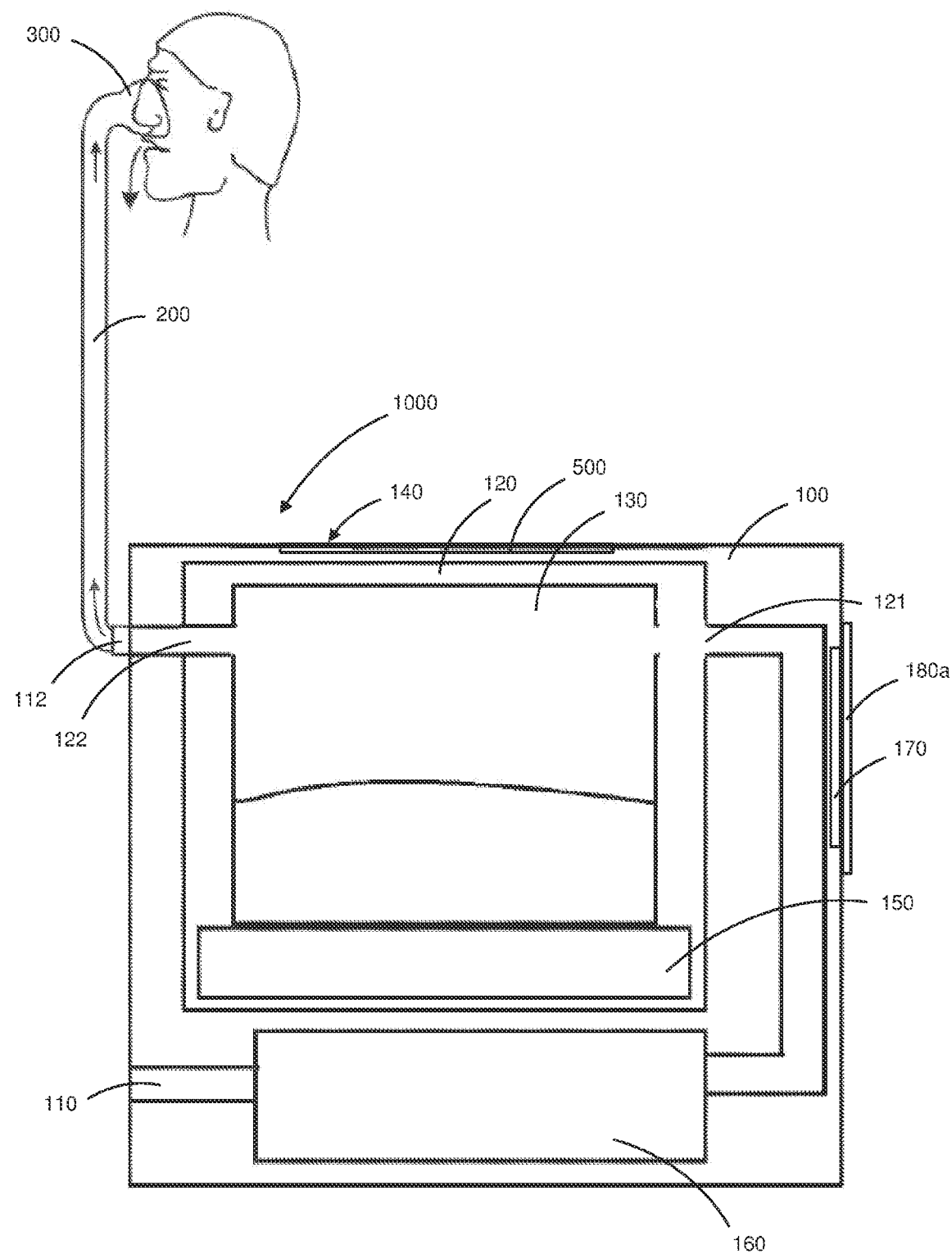
FIG. 1 is a schematic view of a breathing treatment apparatus connected to a user.

FIG. 1 shows one form of breathing treatment apparatus 1000 comprising a body 100 connected to a breathing tube 200, which is connected to an interfacing structure 300 that provides breathing gas to a user of the apparatus. In the embodiment illustrated, the interfacing structure 300 is a nasal mask, but the breathing treatment apparatus 1000 may be used with any suitable form of interfacing structure 300, including a full-face mask, nasal cannula or nasal pillows, for example.

The breathing treatment apparatus 1000 is connected to a user by applying the interfacing structure 300 to the user's airways, such as the mouth and/or nose.

During use, the breathing treatment apparatus MOO may also be connected to a gas source that supplies breathing gas to the apparatus 1000 through an inlet 110 formed in the apparatus body 100.

Figure 2:
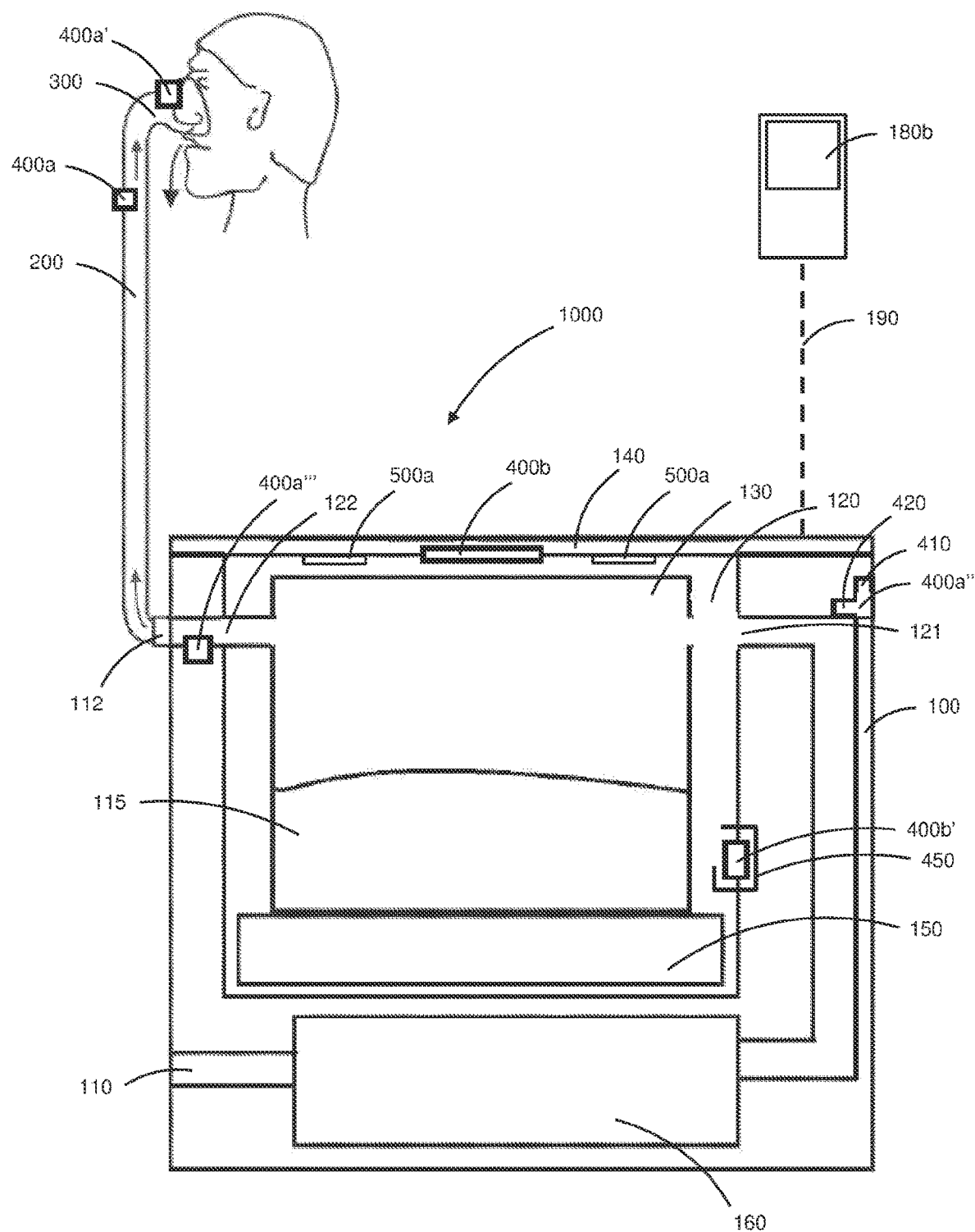
FIG. 2 is a schematic view of the breathing treatment apparatus of FIG. 1 and illustrating possible locations for bacteria sensors.

In one form, as shown in FIGS. 1 and 2, the breathing treatment apparatus 1000 is a CPAP machine that includes a body 100 comprising a humidification compartment 120 that houses a humidification chamber 130 within which a water reservoir 115 may be located. A lid 140 is located on the body and above the humidification compartment to allow easy access to the humidification chamber 130. The apparatus 1000 also comprises a heating element 150, configured to heat water in the humidification chamber 130, and a blower 160. The blower 160 is operated by a motor and may be configured to blow breathing gas from a gas source through an inlet 121 in the humidification compartment 120. As the breathing gas passes through the humidification compartment 120, the gas is humidified with heated water vapour from the humidification chamber 130. The heated, humidified breathing gas then passes through an outlet 122 in the humidification compartment 120 and an outlet 112 in the apparatus body 100 to the breathing tube 200. The breathing gas passes along the breathing tube 200 to the interfacing structure 300 where the gas is inhaled by the user.

The apparatus 1000 may also comprise an electronic control system 170 that connects to a user interface 180. In one form, the user interface 180 may be an inbuilt user interface 180a that forms part of the breathing treatment apparatus 1000 (as shown in FIG. 1). In another form, the user interface may form part of a remote device 600 that is separate from the breathing treatment apparatus 1000 (as shown in FIG. 2), such as a personal computer or a smartphone for example, that communicates with the breathing treatment apparatus through wired or wireless communication channels 190.

The breathing treatment apparatus 1000 may also comprise one or more sensors 400 for detecting microbial growth, such as for sensing bacterial growth and/or sensing fungal growth. The sensors 400 may be electronic sensors, physical sensors, or both.

In preferred forms, the breathing treatment apparatus 1000 comprises one or more bacteria sensors 400, which may be electronic sensors, physical sensors, or both. The bacteria sensors 400 may be configured to sense the presence of bacteria, such as pathogenic bacteria, on or near the sensor. By employing one or more bacteria sensors 400, the apparatus 1000 may be configured to provide a user with an indication of the existence of and/or type of and/or extent of bacteria growth in one or more areas and/or components of the apparatus 1000. The indication of bacterial growth may be of any suitable form or combination of forms, such as a visual and/or audio indication. For example, where the apparatus 1000 comprises one or more electronic sensors 400a, the electronic sensor(s) may be configured to connect to the control system 170. The control system 170 may be configured to receive signals from the electronic sensor(s) that indicate the presence of bacterial growth and, upon receiving such a signal, to issue an indication (such as an alert) to the user interface 180 that indicates: that bacterial growth is present, and/or the type of bacterial growth that is present, and/or the extent of bacterial growth that is present in one or more areas and/or components of the apparatus 1000.

Bacteria sensors 400 may be placed at any suitable location on the apparatus 1000, such as in the interfacing structure 300, in the breathing tube 200, at the outlet of the humidification compartment 122 or the outlet 112 of the body 100 of the apparatus 1000; anywhere within the interior of the body 100 of the apparatus 1000; on the underside of the lid 140, inside the humidification compartment 120, inside the humidification chamber 130, between the blower 160 and the inlet 121 of the humidification compartment; or in any combination of possible locations. Preferably, one or more bacteria sensors are located somewhere along the fluid flow path downstream of the air inlet 121 to the humidification compartment 120. This is because there is a higher risk that pathological bacteria will grow in a warm, humid environment, such as that within the humidification compartment 120, humidification chamber 130, breathing tube 200 or interfacing structure 300. For example, one or more sensors 400 may be located within the humidification compartment 120, such as above and/or within the humidification chamber 130, and/or within the outlet 122 or 112, and/or within the breathing tube 200, and/or within the interfacing structure 300.

The type of sensor used may indicate the best location for the sensor. For example, if the sensor is placed in a difficult to access location, such as in the breathing tube 200, it is preferred that the sensor is an electronic sensor 400a that is in communication with a control system. A sensor in a readily visible location of a component part, such as a sensor in the interfacing structure 300, may be an electronic 400a or physical sensor 400b.

Where the breathing treatment apparatus 1000 comprises more than one electronic sensor 400a, such as the type of sensors disclosed in WO 2016/116535, the sensors 400 may each be provided with an electronic identification (electronic sensor ID) and the control system 170 may be programmed to recognise the electronic sensor ID of each electronic sensor 400a. The control system 170 may also be programmed so that each electronic sensor ID is linked to a positioning code that indicates the position of that sensor 400a in the apparatus 1000. In this arrangement, when an electronic sensor 400a in a certain location, such as in the breathing tube 200, sends a signal to the control system that bacteria is present, the control system may recognise from the sensor ID and positioning code that bacteria has been detected in the breathing tube 200. The control system 170 can then include the sensor positioning information in the indication of bacterial growth or alert that is generated. For example, the control system may generate an indication of bacterial growth in the form of an alert comprising a flashing red light adjacent to a label on the user interface 180 that says 'Breathing Tube". In another form, the control system may cause the user interface 180 to display a message on a screen, such as "It's time to clean the breathing tube", for example. The user interface 180a may be a screen located on the apparatus 1000 or the user interface 180b may be a screen of a remote device, such as a computer or smart phone, for example. After receiving such a message alert, a user will then know that bacteria are present in the breathing tube 200 and the tube 200 needs to be cleaned. As will be appreciated, this is just one example of an indication/alert that may be generated. Any other suitable form of indication or alert may instead be used to indicate to a user that the breathing treatment apparatus 1000 or a component of the apparatus 1000 needs to be cleaned due to the presence of bacteria.

In one form, the apparatus 1000 may comprise more than one sensor 400 in any one location. For example, two sensors may be provided in the mask or in the humidification compartment. The sensors 400 may be of the same type or may be of different types. For example, one sensor may be an electronic sensor 400a and another sensor in the same location may be a physical sensor 400b. Alternatively, both sensors 400 in that location may be electronic sensors 400a or physical sensors 400b. By using two or more sensors 400 in a single location, it is possible to reduce the risk that bacterial growth will not be detected as a result of a faulty sensor.

Preferably, the apparatus 1000 comprises at least one sensor 400 in each bacteria sensitive location of the apparatus 1000. For example, at least one sensor 400 may be provided in the interfacing structure (such as a mask) 300, breathing tube 200, humidification compartment 120, humidification chamber 130 and optionally also at the outlet 112 to the humidification compartment 120.

In another example, the breathing treatment apparatus 1000 may comprise a wick humidifier (such as that described in U.S. application No. 62/491,165), and one or more bacteria sensors may be located on the wick humidifier. In another form, at least a portion of the wick humidifier may comprise a physical sensor attached to or integral with the wick humidifier. The wick humidifier sensor may be used to provide an indication that the wick needs to be cleaned or replaced. In yet another form, the wick humidifier may be held within a wick chamber and one or more bacteria sensors may be located on or in the wick chamber. In another example, the breathing treatment apparatus 1000 may comprise a heat and moisture exchanger (such as that described in PCT application no. PCT/IB2014/065194) located on a gas flow path that extends between a gas inlet to the apparatus and a gas outlet, and may also comprise one or more bacteria sensors located along the gas flow path. In one form, one or more sensors may be located on or close to the heat and moisture exchanger and may be used to indicate that the heat and moisture exchanger needs to be cleaned or replaced.

Figure 3:
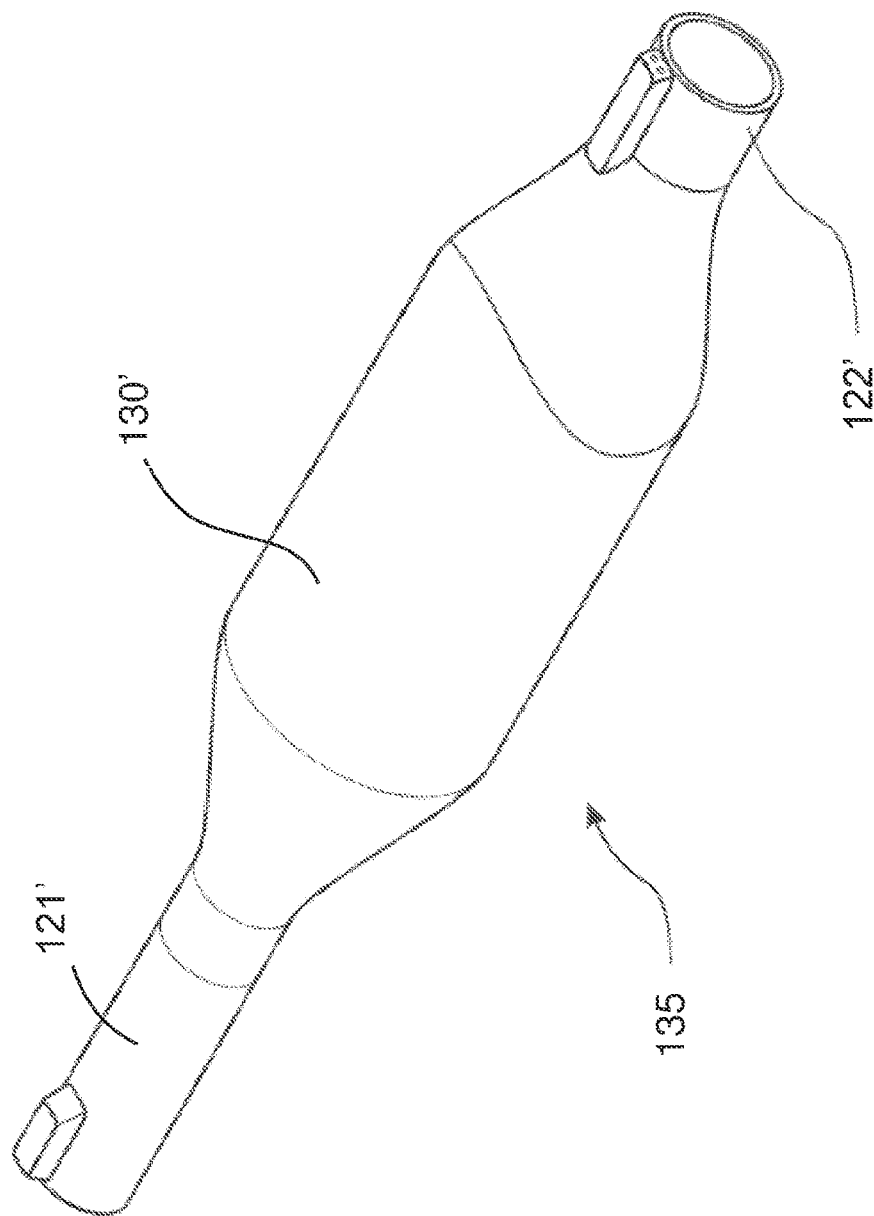
FIG. 3 shows one form of in-line humidifier that may be used with the breathing treatment apparatus of the invention.

In another example, as shown in FIG. 3, the breathing treatment apparatus 1000 may comprise an in-line humidifier 135 comprising a blower (not shown) that blows breathing gas through an inlet 121' at one end of the humidifier 135. The breathing gas is humidified as it passes through a humidification region 130' in the humidifier before exiting an outlet 122' located at another end of the humidifier 135. From the outlet 122', the breathing gas passes along a gas delivery tube to a patient interfacing structure 300. In this configuration, the in-line humidifier 135 may comprise one or more bacteria sensors 400 at any location along the gas flow path between the blower and the outlet 122'.

Figure 4:
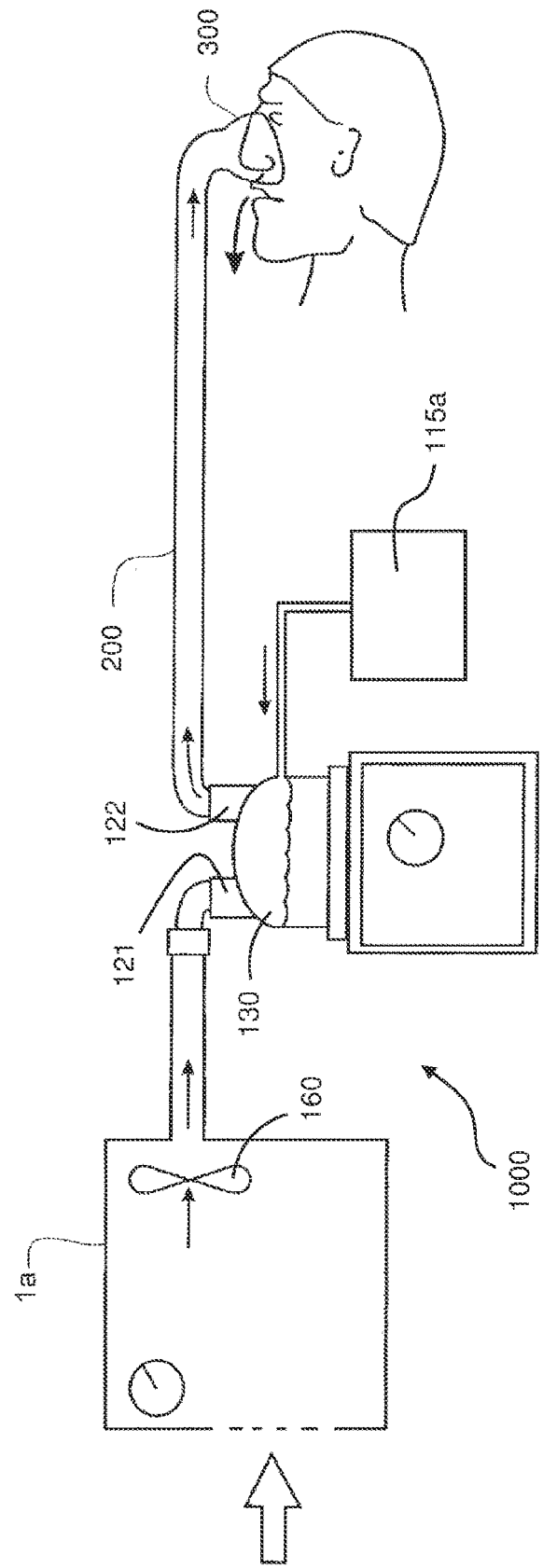
FIG. 4 shows one form of breathing treatment apparatus that comprises an external water reservoir.
Figure 5:
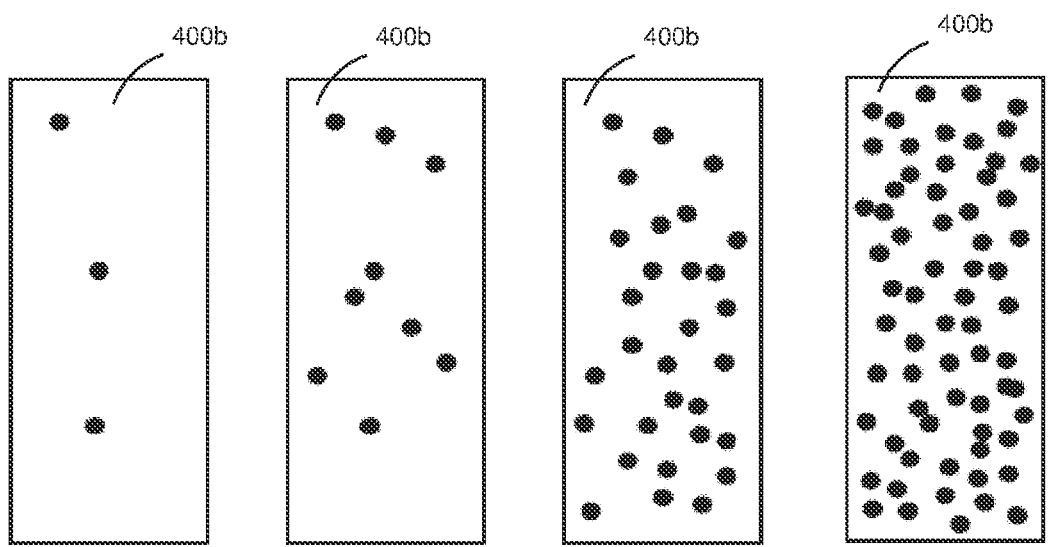
FIGS. 5a to 5d are each plan views of one form of bacteria indicator, showing increasing levels of bacterial growth from FIGS. 5a to 5d.

In yet another example, as shown in FIG. 4, the breathing treatment apparatus 1000 may comprise an external water reservoir 115a configured to hold water in a container that may be separate to the body of the apparatus 1000. In this configuration, one or more bacteria sensors 400 may be located in the external water reservoir 115a. The sensor(s) 400 may be electronic sensor(s) 400a and/or physical sensor(s) 400b. Where the reservoir 115a comprises at least one electronic sensor 400a, the electronic sensor may be configured to send a signal to the control system of the treatment apparatus 1000, or to a control system that forms part of the external water reservoir 115a, when the sensor detects the presence of bacteria.

In another example, the breathing treatment apparatus may comprise a modular sensing unit (such as that described in U.S. patent application Ser. No. 14/515,438 for example). The sensing unit may be positioned at any suitable location along the gas flow stream of the apparatus, such as between the gas delivery conduit and the interfacing structure for example. The sensing unit may comprise one or more bacteria sensors, such as one or more electronic sensors, physical sensors or a combination of both electronic and physical sensors.

By employing multiple sensors 400, the apparatus 1000 may provide indications of bacteria at multiple locations within the apparatus 1000. Therefore, using multiple sensors may indicate that some areas of the apparatus require more frequent cleaning than others. For example, a bacteria sensor 400 located in a mask 300 may indicate that the mask 300 needs to be cleaned, while a bacteria sensor 400 located in the humidification compartment 120 may indicate that the compartment 120 does not need to be cleaned. In this way, the apparatus may be configured to provide a user with a personalised cleaning program where only those parts of the apparatus 1000 that require cleaning need to be cleaned.

In one form, the apparatus 1000 may comprise at least one electronic bacteria sensor 400a configured to detect bacteria on or near the sensor 400a. In some forms, the electronic sensor 400a may be configured to alternatively or additionally detect the type of bacteria and/or the extent of bacterial growth on or near the sensor 400a.

For the sake of simplicity, preferred forms of sensor 400 (both electronic and physical sensors) will be described herein as being configured to detect the presence of bacteria on or near the sensor 400, but it should be appreciated that, this may alternatively or additionally include detecting the type of bacteria and/or the extent of bacteria growth on or near the sensor 400.

In one form, the electronic sensor 400a may be configured to provide a signal to the electronic control system 170 that indicates whether bacteria has or has not been detected. For example, the electronic sensor 400a may be configured to provide the control system 170 with a signal when the presence of bacteria is detected, and/or when a certain type of bacteria is detected, and/or when a certain predetermined threshold level of bacterial population is detected. Alternatively, the control system 170 may be configured to identify when a predetermined threshold level of bacteria has been detected by the sensor 400a such as after receiving a predetermined number of signals from the sensor 400a.

In one form, upon receiving a signal from an electronic bacteria sensor 400, or from a predetermined number of bacteria sensors, or upon receiving a predetermined number of signals from a bacteria sensor or from two or more bacteria sensors, the control system may be caused to change from a normal operating mode to an alert mode. The control system may be configured so that, in the alert mode, the system provides an indication/alert to a user interface 180 that indicates to the user that the apparatus 1000, or a component of the apparatus 1000, needs to be cleaned as a result of bacterial growth. The alert may be any suitable form of indication to a user, including but not limited to a visual display (such as one or more lights, images, words, text message, email, colour changes, or symbols for example), and/or a sound indication (such as one or more beeps for example). Where the user interface 180 is a remote user interface 180b provided on a remote device 600, such as a computer or a smartphone, for example, the control system may be configured to transmit the alert (in the form of an alert signal) to the remote device 600, which may then present the alert on its user interface, such as on a screen 180b, in any suitable form of visual indication, such as an image, words, symbols, colour changes, lights, for example. Alternatively, or additionally the remote device 600 may comprise a user interface 180b configured to present an audio alert, in the form of a noise, which may be of any suitable form, including beeps or other sounds.

In another form, the electronic bacteria sensor 400a may be configured to generate an indication of bacteria detection, which may be a visual or audio indication. Optionally, electronic sensors that are configured to generate a visual alert may be located in areas of the apparatus that are easily visible to a user, such as in the interfacing structure. Additionally or alternatively, physical sensors 400b configured to provide a visual indication of bacterial growth may be located in areas of the apparatus that are easily visible to a user.

An electronic bacteria sensor 400a employed by a breathing treatment apparatus 1000 may be configured to operate continuously (in a continuous mode) or at fixed time intervals (in a periodic mode) to sense the presence of bacteria within the breathing treatment apparatus 1000. Preferably, the control system comprises a clock and is configured to connect to the sensor 400a to determine the mode of operation of the sensor 400a.

In one form, the electronic sensor(s) 400a may comprise a filter to filter out particles that are over a predetermined size.

In one form, an electronic bacteria sensor 400a that may be used with the apparatus 1000 may comprise an electrochemical biosensor 400a'. This form of sensor 400a' may be configured to measure electrical impedance as a method of detecting bacteria in contact with the sensor 400a'. For example, the electrochemical biosensor 400a' may comprise a sensing surface comprising a bio-recognition element and may be configured to produce a signal if the sensor 400a' identifies changes in the electrical properties of the sensing surface, such as changes in impedance, capacitance, or resistance for example. These changes may occur as a result of interactions between the bio-recognition element on the sensor's sensing surface and bacteria to which the sensor 400a' is exposed.

An electronic bacteria sensor 400a may be located at any suitable area of the apparatus 1000. For example, an electronic bacteria sensor 400a may be located inside the humidification compartment 120, such as above or below the water line of the humidification chamber 130. If the sensor 400 is located below the water line, the sensor 400 may be configured to detect the presence of bacteria in the water contacting the sensing surface. If the sensor 400 is located above the water line, the sensor 400 may be configured to detect bacteria in condensation formed on the sensing surface as a result of elevated humidity levels within the humidification compartment 120 during use.

In one form, as shown in FIG. 2, an electronic bacteria sensor 400a is condensate forming sensor 400a" configured to sense bacterial growth in condensation formed on the sensor. The sensor 400a" may be shaped and located so that a first portion/part 410 of the sensor 400a" is exposed to ambient temperature, whilst a sensing surface of a second portion/part 420 of the sensor 400a", which is thermally coupled to the first portion/part 410, is located within the humidification compartment 120 or at any other area within the fluid flow path of the apparatus that is susceptible to bacterial growth, particularly humid areas. For example, the condensation forming sensor may be placed at the inlet 121 (as shown in FIG. 2) or outlet 122 of the humidification compartment 120. In this arrangement, the temperature difference between the second portion 420 of the sensor 400a" and the surrounding humid air in the gas flow path will increase the rate of condensation forming on the sensing surface of the second portion 420 to allow for sensor readings to be obtained more rapidly. In one form, as shown in FIG. 2, the electronic condensate forming sensor 400a" may be substantially L-shaped, or may be formed into a substantially L-shape after being placed on a substantially L-shaped supporting surface. Alternatively, the sensor may be of any suitable shape, or may be placed on a supporting surface of any suitable shape, such that a first portion of the sensor is exposed to ambient temperature and the sensing surface of a second portion of the sensor, which is thermally coupled to the first portion, is located within the humidification compartment or any other humid area within the fluid flow path of the apparatus 1000. The first portion 410 of the condensation forming sensor 400a" may comprise a surface that contacts ambient temperature and the second portion may comprise a sensing surface that extends into the apparatus 1000 in or adjacent to the fluid flow path. The sensor 400a" may be formed of any suitable material that encourages condensation to form on the sensing surface of the second portion of the sensor. In one form, the first and second portions 410, 420 may be formed of metal. For example, the condensation forming electronic sensor 400a" may comprise a metal strip having a portion/part that forms the first portion 410 of the sensor and another portion/part that forms the second portion 420 of the sensor 400a". The change in temperature between the second portion 420 and the surrounding air in the gas flow path may cause condensation to form more readily on the sensing surface of the second portion 420.

In one form, the electronic sensor 400a may be in form of a smell sensor 400a''' that is configured to provide an indication of the presence of bacteria when the sensor 400a''' smells specific odours associated with the presence of bacteria. Smell sensors 400a''' such as the Figaro TGS 2602 comprise a semi-conductor layer formed on a substrate. In the presence of a detectable gas, the conductivity of the sensor 400a''' varies, depending on the concentration of the detectable compound in the gas. These sensors 400a''' may be calibrated to have reasonably high sensitivity to low concentrations of odorous gases that are associated with bacterial populations. Upon detection of these gases, the sensor 400a''' may be configured to provide a signal to the control system that bacteria has been detected and/or that a predetermined level of bacteria has been detected and/or that a certain type of bacteria has been detected. The control system may then generate an indication or alert, such as a visual indication on a user interface 180, or an audio indication.

In one form, the breathing treatment apparatus 1000 may comprise one or more physical bacteria sensors 400b that are configured to detect the presence of bacteria in the apparatus 1000 and to provide a visual indication of the presence of bacteria and/or the type of bacteria and/or the extent of bacterial growth on the sensor 400b.

In one form, the physical sensor 400b comprises a body, such as a substrate, that is configured to provide a visual indication of bacteria growing on the sensor body. For example, the body may comprise a bacteria sensitive surface or material having physical properties that cause a change to the appearance of the sensor 400b when bacteria grow on the sensor, or when bacterial growth on the sensor reaches a threshold level or when a certain type of bacteria grows on the sensor 400b. In one form, the physical sensor 400h comprises a body comprising a first flexible plastic layer and a second layer comprising a nutrient containing filter paper attached to the plastic layer. The nutrient containing filter paper layer may form a bacteria sensitive surface to the sensor that is configured to show coloured areas or spots, such as red spots, when aerobic bacteria forms on the sensor 400b. The number of spots, together with the extent of background colouring/reddening can be used to quantitatively measure microbial growth on the sensor 400b.

In one form, a chemical may be added to material forming the body of the sensor 400b to provide a material that will produce a visual colour indication of bacterial growth when bacteria are present on the sensor, or when bacterial growth reaches a threshold level, or when a certain type of bacteria is present on the sensor 400b.

In another form, a coating is provided on one or both sides of the body of the sensor 400b and is configured to allow bacteria to grow on the coating and to provide a visual indication of the presence of bacteria on the sensor 400b.

FIGS. 5a to 5d illustrate one form of physical bacteria sensor 400b that comprises a strip of material that has been configured to provide a visual indication of bacterial growth on the sensor 400b. The physical sensors 400b shown in FIGS. 5a to 5d demonstrate increasing levels of bacterial growth from FIG. 5a to FIG. 5d.

In one form, a reactant may be impregnated into a material, such as filter paper, forming the body of the sensor or provided on the body of the sensor 400h, where the reactant is configured to cause a colour change in the filter paper when bacteria grow on the paper. For example, a Bradford assay may be used as the visual indication of bacterial growth. In this form, a material may be impregnated with a dye, such as Coomassie Brilliant Blue G-250 for example. When certain acidic conditions are met, due to the growth of bacteria, the sensor 400b may change from red to blue as the dye binds to the protein being assayed. Although a physical bacteria sensor 400b may be placed at any suitable location within the breathing treatment apparatus 1000, it is preferred to place a physical bacteria sensor on the underside of the lid 140 of the treatment apparatus body 100, which may also form the lid of the humidification compartment 120, as shown in FIG. 2. In one for the lid 140 comprises a fully or at least partially transparent window beneath which the physical sensor 400b is located so that a user can view the sensor through the window.

When a user sees a discoloured physical sensor 400b, the user will know that it is necessary to clean at least the component of the apparatus 1000 where the sensor 400h is located. The user then removes the infected sensor 400b, cleans that component of the apparatus 1000, and places a new sensor 400b in the component.

It is appreciated that some users may prefer not to see bacteria growing on a physical sensor 400b. Therefore, in one form, the sensitivity of the physical sensor 400h may be configured so that bacterial colonies are not visible to the naked eye and may instead be analysed by an analyser. The analyser may form part of the breathing treatment apparatus 1000 or may form part of a remote device 600 that is separate to the apparatus 1000. The analyser may be configured to identify whether bacteria is growing on a physical sensor and/or to identify whether the bacteria exceeds a predetermined threshold and/or to identify the type of bacteria. In one form, the analyser may comprise a smartphone that comprises a bacteria analysis app or similar electronic analyzing software. The smartphone may comprise a magnifying lens 610 connected to the smartphone camera. In one form, the magnifying lens may comprise a microscope. The user may be able to detect the presence of bacteria simply by looking at the physical sensor 400b through the magnifying lens or by photographing the physical sensor with the smartphone camera and magnifying lens. Once the user detects the presence of bacteria, the user knows to remove the infected sensor 400b, clean the relevant component of the apparatus 1000, and replace the sensor 400b in the component.

In one form, as shown in FIG. 2, the breathing treatment apparatus 1000 may comprise a cartridge 450 in which a removeable physical sensor 400b' may be held. For example, the cartridge 450 may comprise a frame having an opening, such as a slot at one end, through which the sensor 400b' can be inserted and removed. The frame may be configured so that at least a portion of the sensor 400b' is exposed. In one form, the sensor may be removable from the cartridge. For example, the cartridge may be configured to attach to the apparatus 1000 at a desired location and may comprise a removable cassette in which a sensor 400b' is held. The sensor 400h' may be replaced by removing the cassette from the cartridge, removing the infected sensor from the cassette and replacing with a clean sensor, and then returning the cassette to the cartridge. In another form, the entire cassette or cartridge may be replaced. The cartridge may be configured to be fixed in location or the cartridge may be configured to detachably attach to the apparatus 1000 so that it can be discarded and replaced or moved to a different location if desired.

Figure 6:
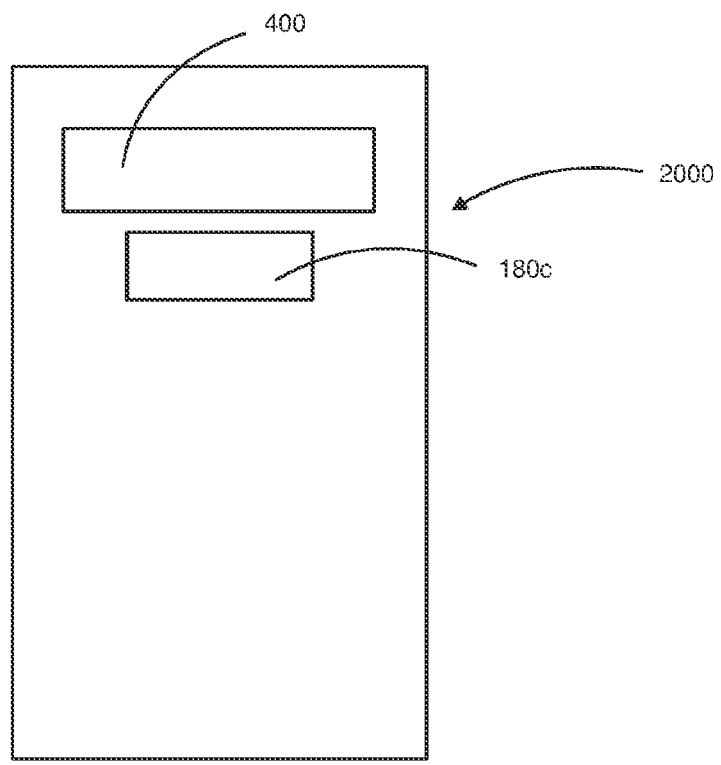
FIG. 6 is a schematic view of one form of sensing tool.

In another form, as shown in FIG. 6, a remote device in the form of a portable sensing tool 2000 is configured to receive one or more bacteria sensors 400. The sensing tool 2000 may comprise one or more electronic sensors 400a, physical sensors 400b, or any combination of sensors configured to detect the presence of bacteria. The tool 2000 is configured to sense bacteria in a breathing treatment apparatus 1000 after exposing the one or more sensors on the tool to a bacteria sensitive location of the apparatus 1000. Preferably, the sensor(s) is/are exposed to the bacteria sensitive location for a minimum predetermined period of time to ensure sufficient exposure of the sensor(s) to any bacteria that may be present. In one form, the tool may comprise a control system having a clock and a user interface 180c. The user may input a start period into the user interface 180c and the clock may count a predetermined time from the start period. When the predetermined time is reached, the control system may provide a 'sensing complete' indication, such as via the user interface 180c, which indicates to a user, via a visual or audio indication, that the bacteria sensing stage has been completed and the tool may be removed from the apparatus. To avoid confusion, it is preferred that the sensing complete indication is different from any indication that may subsequently issue from the tool to show the presence of bacteria in the apparatus. For example, if one or more electronic sensors are used with the tool, the sensing complete indication may be an audio indication or a flashing green light and the bacterial growth indication may be a flashing red light.

In one form, a user may use the portable sensing tool 2000 by taking a water sample from the humidification chamber 130 and exposing the appropriate sensor(s) 400 on the tool to the water sample to detect the presence of bacteria. For example, a user may take a water sample with a sterile device, such as a pipette and may place a drop of water onto the sensing surface of an electronic sensor 400a or physical sensor 400b located on the tool 2000. A physical sensor 400b will be able to provide a relatively quick visual indication of the presence of bacteria and the user will then know whether the breathing treatment apparatus 1000 needs to be cleaned. If the sensing tool 2000 comprises an electronic sensor 400a, the sensor 400a may be configured to generate a visual and/or audio indication that bacteria is present. For example, the sensor 400a may comprise a light that lights up, or the sensor may be configured to generate a sound, when the sensor 400a detects the presence of bacteria.

Figure 7:
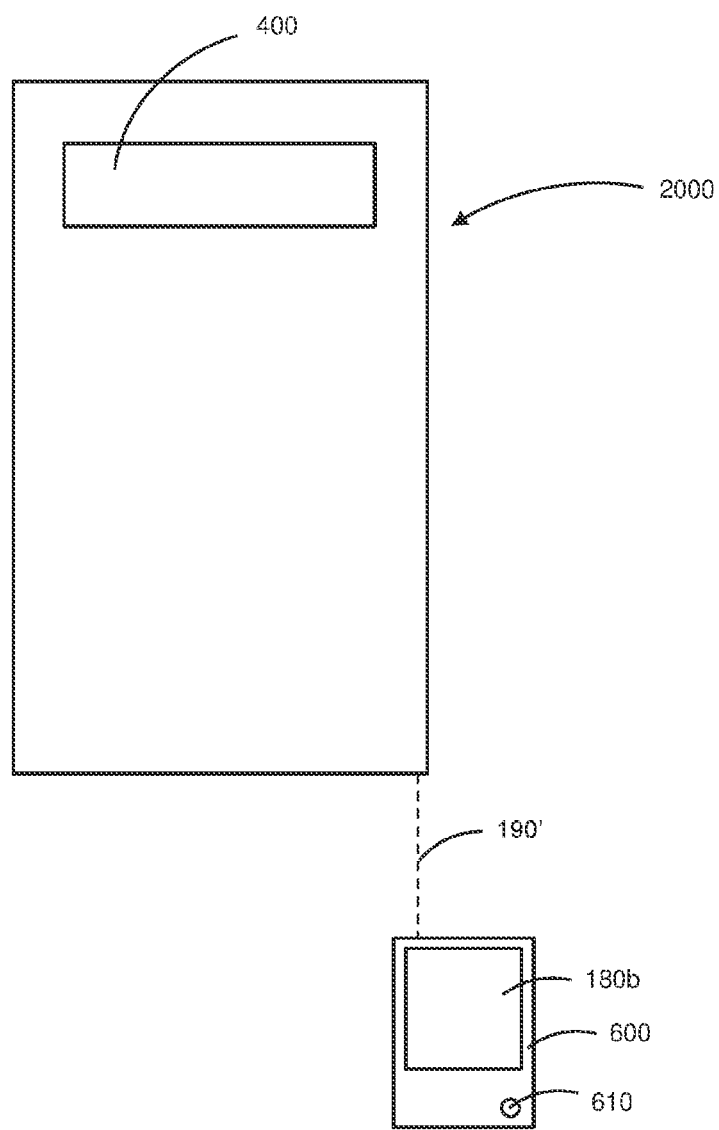
FIG. 7 is a schematic view of another form of sensing tool.

Alternatively, the sensing tool 2000 may comprise a control system and one or more electronic sensors 400a on the tool may be connected to the control system. The control system may be configured to receive a signal from the electronic sensor(s) 400a and to generate an indication/alert via a user interface 180 if the sensor 400a signal indicates that bacteria is present in the apparatus 1000. The user interface 180 may form part of the sensing tool 2000, as shown in FIG. 6, or the user interface 180b may be provided on a remote device 600, such as a computer or smart phone, that communicates with the sensing tool 2000 through wired or wireless communication channels 190', as shown in FIG. 7. Again, the alert, generated may be a visual and/or audio alert.

In one form, the sensing tool 2000 or a remote device 600 may comprise a camera or magnifying lens 610 that allows a user to identify the presence of bacteria on a physical sensor 400b that has been desensitized so that bacterial colonies are not visible to the naked eye.

When the user receives an indication that bacteria are present in the breathing treatment apparatus 1000 and/or that certain types of bacteria are present and/or that certain levels of bacteria are present, the user should then clean the apparatus 1000 or at least clean that component of the apparatus 1000 in which the sensor 400 that detected the bacteria is located.

After the cleaning step, the user may reset the sensor 400, either manually (such as by replacing a physical sensor for example) or via the user interface 180 (if the sensor is an electronic sensor), which may cause the control system to be reset to normal operating mode. In another form, the breathing treatment apparatus 1000 may be configured to detect a sterilisation event so that the control system may automatically reset to the normal operating mode itself. For example, the apparatus 1000 may comprise an in-built sterilisation system 500 that automatically sterilises the apparatus 1000 or particular components of the apparatus 1000 when the control system receives a signal from a sensor that bacterial growth is present or when the control system generates an indication/alert of bacterial growth after receiving such a signal or signals. In one form, the sterilisation system 500 comprises a series of ultra-violet lights 500a, such as UV LED lights. The lights may be strategically located at any suitable location in the apparatus 1000, such as in the interior of the body 100 of the apparatus 1000. In one form, the ultra-violet lights 500a are located within the humidification compartment 120, as shown in FIG. 2. When the control system 170 receives a signal from one or more sensors 400a that causes the control system to identify the presence of bacteria, or to identify the presence of a certain type of bacteria, or to identify that a predetermined threshold of bacteria levels have been met, the control system may generate an alert to a user via a user interface 180 and/or the control system may activate the sterilisation system 500.

If the control system 170 activates the sterilisation system 500, the ultra-violet lights 500a are turned on to kill bacteria within the body 100 of the apparatus 1000 or at any other location in the apparatus 1000 where the ultra-violet lights are located. After the sterilisation process, the control system 170 may automatically reset to the normal operating mode.

However, if the bacteria are growing in water within the water reservoir in the humidification chamber 130, it is possible that even with UV sterilisation, the bacteria will grow back relatively quickly until the water is replaced and the water reservoir and humidification chamber are manually cleaned. For this reason, the control system 170 may be programmed to provide a 'cleaning required' indication to a user interface 180. The 'cleaning required' indication may be a visual and/or audio indication to a user that the apparatus 1000 or at least one or more particular components of the apparatus 1000 need to be manually cleaned. If only certain components of the apparatus 1000 need to be manually cleaned, the control system may also cause the user interface 180 to indicate which components require manual cleaning.

In one form, the in-built sterilisation system 500 may be configured to be manually activated only or may be configured to activate automatically and manually. A manually activated sterilisation system may be useful where physical sensors 400b indicate the presence of bacteria to the extent that the apparatus 1000 or a component of the apparatus 1000 needs to be sterilised. In such a scenario, the user can then remove and replace the bacteria infected physical sensor 400b with a clean sensor 400b and can then activate the sterilisation system manually.

By using one or more bacteria sensors 400 in a breathing treatment apparatus 1000, or by using a sensing tool 2000 with a breathing treatment apparatus 1000, it is possible for the user to follow a cleaning schedule in which components of the breathing treatment apparatus 1000 are cleaned when necessary rather than according to a fixed, arbitrarily created cleaning regime. In this way, cleaning schedules of breathing treatment apparatuses 1000 can be more personalised and can reflect the duration and frequency of use of the apparatus. As a result, cleaning of the apparatus 1000 may be less onerous and so a user may be more likely to use the apparatus regularly and thereby comply with breathing treatment therapy requirements.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the scope of the invention.

What is claimed is:

1. A breathing treatment apparatus for delivering breathing gas to a user, wherein the breathing treatment apparatus comprises:
   at least one bacteria sensor configured to detect bacteria in the breathing treatment apparatus and to provide an indication to the user that bacteria is present;
   wherein the at least one bacteria sensor is a physical sensor configured to indicate a presence of bacteria on the at least one bacteria sensor; and
   wherein the breathing treatment apparatus comprises a cartridge configured to removably hold the physical sensor.

2. The breathing treatment apparatus of claim 1, wherein the at least one bacteria sensor comprises a body configured to provide a visual indication of bacterial growth on the body and/or comprises a bacteria sensitive surface.

3. The breathing treatment apparatus of claim 2, wherein the bacteria sensitive surface is configured to show colored areas when aerobic bacteria forms on the at least one bacteria sensor.

4. The breathing treatment apparatus of claim 2, wherein the body comprises a nutrient containing filter paper.

5. The breathing treatment apparatus of claim 4, wherein the body further comprises a first layer and a second layer, and wherein the nutrient containing filter paper is attached to at least one of the first layer and the second layer and wherein at least one of the first layer and the second layer is a flexible plastic layer.

6. The breathing treatment apparatus of claim 1, wherein the physical sensor is removably attached to the breathing treatment apparatus.

7. The breathing treatment apparatus of claim 1, wherein the physical sensor comprises a strip of material.

8. The breathing treatment apparatus of claim 1, wherein the at least one bacteria sensor is positioned on a visible location of a component of the breathing treatment apparatus.

9. The breathing treatment apparatus of claim 1, wherein more than one of the at least one bacteria sensor are positioned at a location.

10. The breathing treatment apparatus of claim 9, wherein more than one of the at least one bacteria sensor are of a same type or wherein more than one of the at least one bacteria sensor are of different types.

11. The breathing treatment apparatus of claim 1, wherein the at least one bacteria sensor is configured to indicate to the user that the breathing treatment apparatus requires cleaning.

12. The breathing treatment apparatus of claim 1, wherein the breathing treatment apparatus comprises a sterilisation system for sterilising an interior of the breathing treatment apparatus, the sterilisation system comprising a manual control that the user may operate to activate the sterilisation system manually.

13. The breathing treatment apparatus of claim 1, wherein the breathing treatment apparatus is an integrated CPAP and humidifier.

14. The breathing treatment apparatus of claim 1, wherein the breathing treatment apparatus is a modular CPAP and humidifier.

15. The breathing treatment apparatus of claim 1 that comprises a fluid flow path from a blower to an inlet of a humidification compartment.

16. The breathing treatment apparatus of claim 15, wherein the at least one bacteria sensor is located in the fluid flow path.

17. The breathing treatment apparatus of claim 1, wherein the at least one bacteria sensor is located under a fully or at least partially transparent window.

18. The breathing treatment apparatus of claim 15, wherein the breathing treatment apparatus further comprises a humidification chamber and an outlet connected to a delivery tube that connects to an interface structure, and wherein the at least one bacteria sensor is located in the inlet of the humidification compartment, the humidification compartment, the humidification chamber, the outlet, the delivery tube, or the interface structure.

19. The breathing treatment apparatus of claim 1, wherein the at least one bacteria sensor is located on a lid of the breathing treatment apparatus.

* * * * *